United States Patent
Chang et al.

(10) Patent No.: US 9,389,506 B2
(45) Date of Patent: *Jul. 12, 2016

(54) PHOTORESIST HAVING IMPROVED EXTREME-ULTRAVIOLET LITHOGRAPHY IMAGING PERFORMANCE

(71) Applicant: Taiwan Semiconductor Manufacturing Company, Ltd., Hsin-Chu (TW)

(72) Inventors: Shu-Hao Chang, Taipei (TW); Tsiao-Chen Wu, Hsinchu County (TW); Chih-Tsung Shih, Hsinchu (TW)

(73) Assignee: Taiwan Semiconductor Manufacturing Company, Ltd., Hsin-Chu (TW)

(*) Notice: Subject to any disclaimer, the term of this patent is extended or adjusted under 35 U.S.C. 154(b) by 0 days.

This patent is subject to a terminal disclaimer.

(21) Appl. No.: 14/742,862

(22) Filed: Jun. 18, 2015

(65) Prior Publication Data

US 2015/0286138 A1    Oct. 8, 2015

Related U.S. Application Data

(63) Continuation of application No. 13/033,725, filed on Feb. 24, 2011, now Pat. No. 9,081,280.

(51) Int. Cl.

| | |
|---|---|
| *G03F 7/004* | (2006.01) |
| *G03F 7/038* | (2006.01) |
| *G03F 7/039* | (2006.01) |
| *C07C 309/65* | (2006.01) |
| *C07C 381/12* | (2006.01) |
| *G03F 7/20* | (2006.01) |

(52) U.S. Cl.
CPC .............. *G03F 7/038* (2013.01); *C07C 309/65* (2013.01); *C07C 381/12* (2013.01); *G03F 7/0045* (2013.01); *G03F 7/0395* (2013.01); *G03F 7/0397* (2013.01); *G03F 7/20* (2013.01)

(58) Field of Classification Search
CPC ... G03F 7/0045; G03F 7/0395; G03F 7/0397; C07C 309/65; C07C 381/12
USPC .................................. 430/270.1, 319; 558/44
See application file for complete search history.

(56) References Cited

U.S. PATENT DOCUMENTS

| | | | |
|---|---|---|---|
| 7,459,260 B2 | 12/2008 | Chandhok et al. | |
| 7,569,324 B2 | 8/2009 | Kobayashi et al. | |

(Continued)

OTHER PUBLICATIONS

Holger Kierey et al., "EUV Spectral Purity Filter: Optical and Mechanical Design, Gratings Fabrication, and Testing", Advances in Mirror Technology for X-Ray, EUV Lithography, Laser and Other Applications, Proceedings of SPIE vol. 5193, pp. 70-78.

*Primary Examiner* — Amanda C Walke
(74) *Attorney, Agent, or Firm* — Haynes and Boone, LLP (57) ABSTRACT

Provided herein is a photoresist compound with improved extreme-ultraviolet lithography image performance. The photoresist includes a polymer that is free of an aromatic group and a photo acid generator (PAG) free of aromatic groups. The PAG includes an anion component and a cation component, wherein the anion component has one of the several specified chemical formulas and the cation component also has a specified chemical formula. The anion component includes a material selected from the group consisting of methyl and ethyl and the cation component includes a material selected from the group consisting of: an alkyl group, an alkenyl group, and an oxoalkyl group.

20 Claims, 5 Drawing Sheets

(56) References Cited

U.S. PATENT DOCUMENTS

| | | |
|---|---|---|
| 7,666,967 B2 | 2/2010 | Harada et al. |
| 7,691,561 B2 | 4/2010 | Taniguschi et al. |
| 7,718,342 B2 | 5/2010 | Funatsu et al. |
| 7,785,767 B2 | 8/2010 | Kanda |
| 7,897,821 B2 | 3/2011 | Nagai et al. |
| 7,955,780 B2 | 6/2011 | Kato et al. |
| 8,007,981 B2 | 8/2011 | Watanabe et al. |
| 8,012,669 B2 | 9/2011 | Shimizu et al. |
| 8,541,160 B2 | 9/2013 | Shibuya |
| 2002/0051932 A1 | 5/2002 | Brainard et al. |
| 2003/0113658 A1 | 6/2003 | Ebata et al. |
| 2005/0008864 A1 | 1/2005 | Ingen Schenau et al. |
| 2007/0172769 A1 | 7/2007 | Kanna et al. |
| 2008/0102407 A1 | 5/2008 | Ohsawa et al. |
| 2008/0118860 A1 | 5/2008 | Harada et al. |
| 2008/0206669 A1 | 8/2008 | Kato et al. |
| 2009/0035692 A1 | 2/2009 | Tarutani et al. |
| 2009/0233238 A1 | 9/2009 | Hsu et al. |
| 2010/0255419 A1 | 10/2010 | Kodama et al. |
| 2011/0229832 A1 | 9/2011 | Kamimura et al. |
| 2012/0052440 A1 | 3/2012 | Yoshida et al. |
| 2014/0178821 A1 | 6/2014 | Kawaue et al. |

PHOTORESIST HAVING IMPROVED EXTREME-ULTRAVIOLET LITHOGRAPHY IMAGING PERFORMANCE

PRIORITY DATA

The present application is a continuation application of U.S. patent application Ser. No. 13/033,725 filed Feb. 24, 2011, entitled "PHOTORESIST HAVING IMPROVED EXTREME-ULTRAVIOLET LITHOGRAPHY IMAGING PERFORM," which is hereby incorporated by reference in its entirety.

BACKGROUND

The semiconductor integrated circuit (IC) industry has experienced rapid growth. Technological advances in IC materials and design have produced generations of ICs where each generation has smaller and more complex circuits than the previous generation. However, these advances have increased the complexity of processing and manufacturing ICs and, for these advances to be realized, similar developments in IC processing and manufacturing are needed. In the course of integrated circuit evolution, functional density (i.e., the number of interconnected devices per chip area) has generally increased while geometry size (i.e., the smallest component (or line) that can be created using a fabrication process) has decreased.

Various photolithography processes may need to be performed to fabricate these increasingly small ICs. A photoresist material is used in the photolithography processes. In particular, the photoresist material is often used to pattern the ICs and is removed after the patterning is complete. However, as lithography processes continue to evolve, existing photoresist materials may have performance shortcomings. For example, an Extreme Ultraviolet (EUV) Lithography process may lack spectral purity for its light sources, meaning the light sources may produce undesirable out-of-band radiation, for example radiation having a bandwidth between 140 nanometers (nm) and 400 nm. Existing photoresist materials may be sensitive to the out-of-band radiation and may absorb such radiation. This would result in reduced contrast and hence degradation of imaging performance.

Therefore, while existing photoresist materials have been generally adequate for their intended purposes, they have not been entirely satisfactory in every aspect.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

It is to be understood that the following disclosure provides many different embodiments, or examples, for implementing different features of the invention. Specific examples of components and arrangements are described below to simplify the present disclosure. These are, of course, merely examples and are not intended to be limiting. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Various features may be arbitrarily drawn in different scales for the sake of simplicity and clarity.

Figure 1:
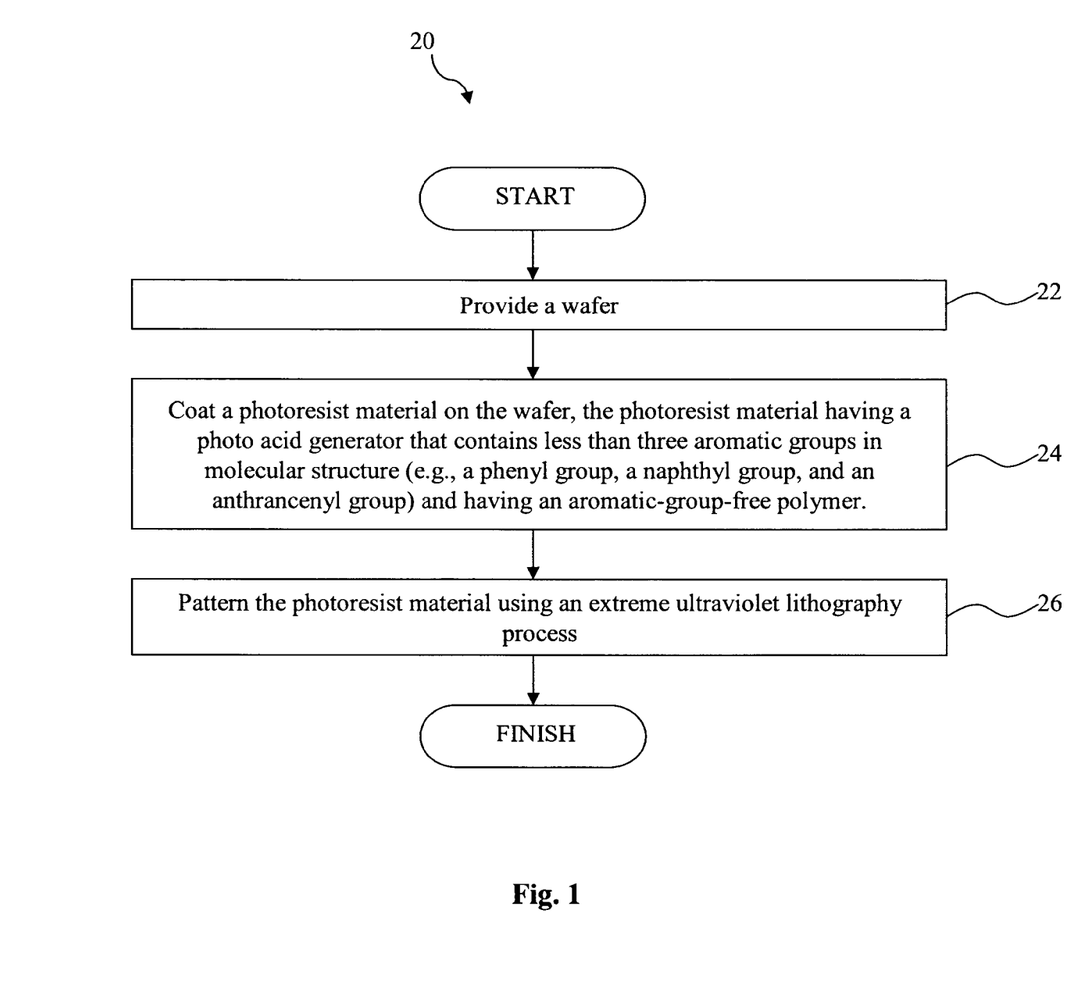
FIG. 1 is a flowchart illustrating a method for fabricating a semiconductor device according to various aspects of the present disclosure.

Illustrated in FIG. 1 is a flowchart of a method 20 of patterning wafer according to various aspects of the present disclosure. The method 20 includes block 22 in which a wafer is provided. The method 20 includes block 24 in which a photoresist material is formed over the wafer. The photoresist material has a photo acid generator that contains less than three aromatic groups in molecular structure (e.g., a phenyl group, a naphthyl group, and an anthrancenyl group) and has an aromatic-group-free polymer. The method 20 includes a block 26 in which the photoresist material is patterned using an extreme ultraviolet lithography process. It is understood that additional processes may be performed before, during, or after the blocks 22-26 of the method 20 to complete the fabrication of the semiconductor device.

Figure 2:
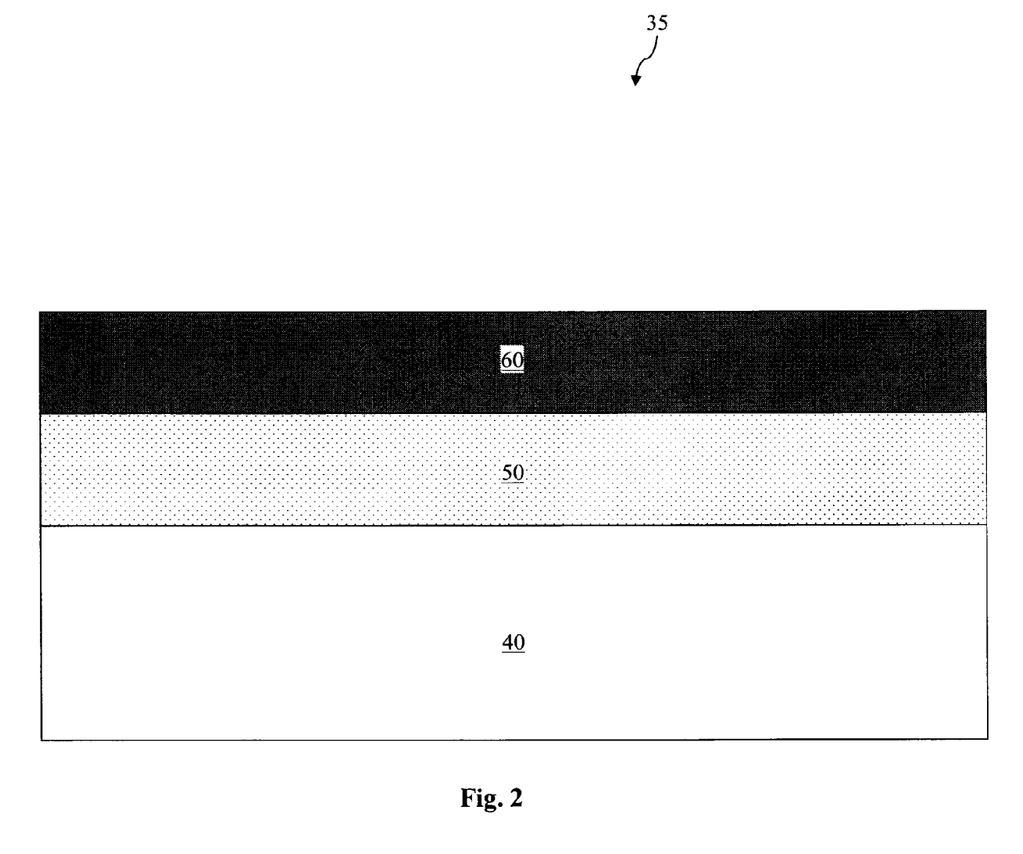
FIGS. 2-4 are diagrammatic cross-sectional side views of a semiconductor device at various stages of fabrication in accordance with various aspects of the present disclosure.
Figure 3:
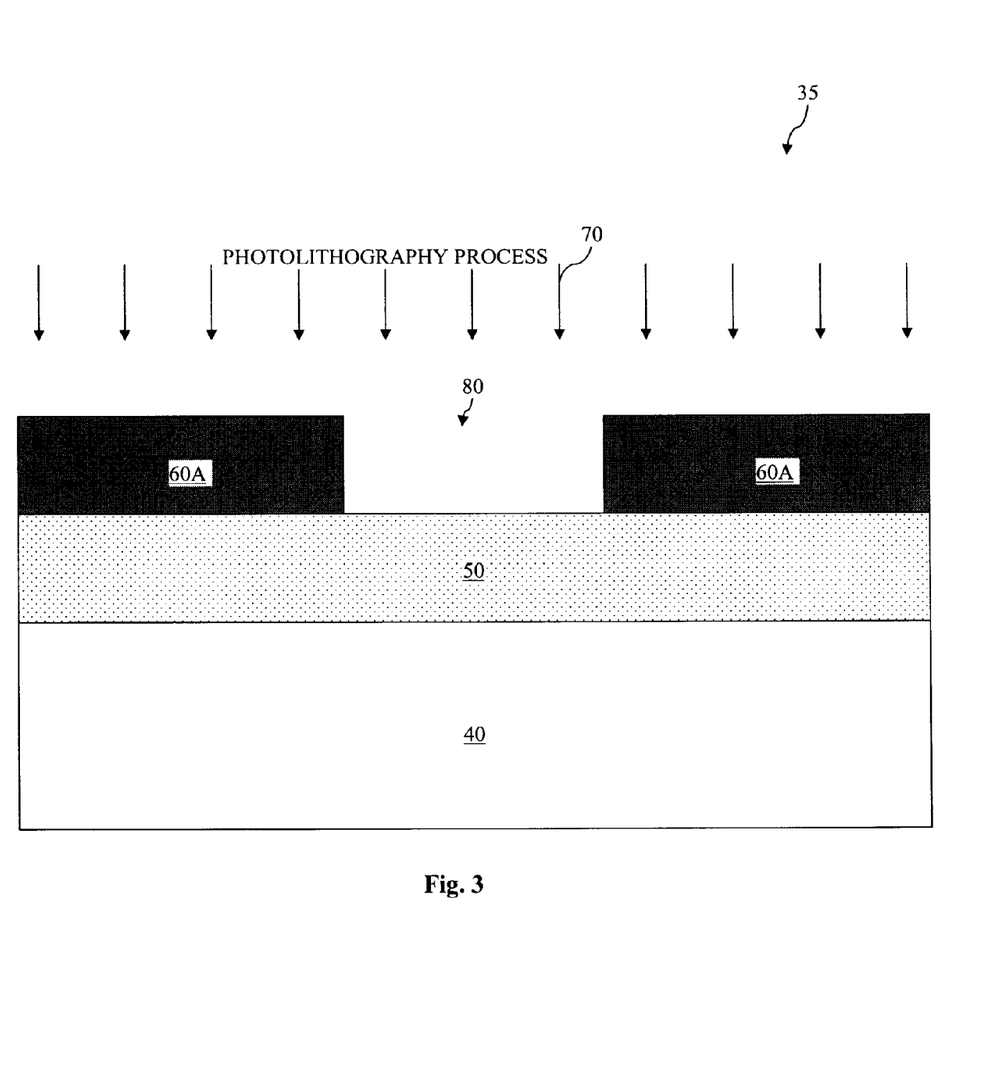

FIGS. 2-3 are diagrammatic fragmentary cross-sectional side views of a semiconductor device 35 at various stages of fabrication in accordance with various aspects of the present disclosure. The semiconductor device 35 may include an integrated circuit (IC) chip, system on chip (SoC), or portion thereof, and may include various passive and active microelectronic devices such as resistors, capacitors, inductors, diodes, metal-oxide semiconductor field effect transistors (MOSFET), complementary metal-oxide semiconductor (CMOS) transistors, bipolar junction transistors (BJT), laterally diffused MOS (LDMOS) transistors, high power MOS transistors, or other types of transistors.

Referring to FIG. 2, the semiconductor 35 includes a substrate 40. The substrate 40 is a silicon substrate doped with a p-type dopant such as boron (for example a p-type substrate). Alternatively, the substrate 40 could be another suitable semiconductor material. For example, the substrate 40 may be a silicon substrate that is doped with an n-type dopant such as phosphorous or arsenic (an n-type substrate). The substrate 40 could include other elementary semiconductors such as germanium and diamond. The substrate 40 could optionally include a compound semiconductor and/or an alloy semiconductor. Further, the substrate 40 could include an epitaxial layer (epi layer), may be strained for performance enhancement, and may include a silicon-on-insulator (SOI) structure.

A material layer 50 is formed over the substrate 40. In an embodiment, the material layer 50 includes a dielectric material, such as silicon oxide or silicon nitride. In another embodiment, the material layer 50 includes metal. In yet another embodiment, the material layer 50 includes a semiconductor material. It is understood that the substrate 40 and the material layer 50 may each include other suitable material compositions in other embodiments.

A photoresist material 60 is formed over the material layer 50. In the embodiment shown in FIG. 2, the photoresist material 60 includes a positive photoresist, but it is understood that the photoresist material 60 may be a negative photoresist in alternative embodiments. The photoresist material 60 is formed by a spin-coating process. The photoresist material 60 includes a polymer, photo acid generators (PAG), quenchers etc. In an embodiment, the photo acid generator is bonded to the polymer. In a subsequent photolithography process (described in more detail later), photons induce decomposition of the PAG. As a result, a small amount of acid is formed, which further induces a cascade of chemical transformations in the photoresist material 60. The photoresist material 60 may also optionally include a quencher that is disposed within the photoresist material 60 in order to improve critical dimension (CD) control.

Conventional photoresist materials contain aromatic groups such as a phenyl group, a naphthyl group, and/or an anthrancenyl group. These aromatic groups were needed to provide stability to conventional photoresist materials. For example, a PAG may have a cation that needs electrons to stabilize the structure. The aromatic groups are electron-rich and therefore provide stability to the cation. However, the aromatic groups also absorb radiation having bandwidths that are out of a desired bandwidth of an extreme ultraviolet (EUV) band. For example, radiation having a bandwidth in a range between about 140 nanometers (nm) to about 400 nm is considered un-desirable out-of-band radiation for EUV lithography processes. The absorption of such out-of-band radiation results in reduced contrast and hence degradation of imaging performance of conventional photoresist materials.

In contrast, the PAG of the photoresist material 60 of the present disclosure contain less than three aromatic groups. In an embodiment, the polymer of material 60 doesn't have any aromatic group and the PAG of the photoresist material 60 includes less than three aromatic groups. The various embodiments of the PAG and the polymer of the photoresist material 60 are discussed in more detail below.

In an embodiment, the PAG of the photoresist material 60 includes an anion having one of the following chemical formulas (also referred to as chemical structure, structural formula, or structural diagrams):

where $R^1$ includes hydrogen, fluorine, methyl, ethyl, or trifluoromethyl, or combinations thereof. In an embodiment, the PAG of the photoresist material 60 includes a cation having one of the following chemical formulas:

where each $R^2$ includes an alkyl group, an alkenyl group, or an oxoalkyl group, or combinations thereof. $R^2$ may be substituted or unsubstituted, and may be straight or branched. In an embodiment, at least two of $R^2$ are bonded together to form a ring with the sulfur atom/ion ($S^+$).

In an embodiment, the polymer of the photoresist material 60 includes recurring units of a compound represented by one of the chemical formulas below:

wherein $R^1$ includes hydrogen, fluorine, methyl, ethyl, or trifluoromethyl, or combinations thereof. $R^3$ includes a labile group, or hydrogen, a fluoroalkyl group, a fluoroalcohol-containing substituent group, or combinations thereof. $R^4$ includes a lactone-structure-containing substituent group.

Referring now to FIG. 3, a photolithography process 70 is performed on the photoresist material 60 to form a patterned photoresist layer 60A having an opening 80. In an embodiment, the photolithography process 70 includes an EUV lithography process. The EUV lithography process uses a light source (or illumination source) that has a wavelength that is about 13.5 nm. The light sources exposes a predetermined region (corresponding to the opening 80) of the photoresist material 60, while other regions of the photoresist material 60 are protected through the use of a photomask (not illustrated). Since the photoresist material 60 is almost free of aromatic groups, substantially almost no out-of-band radiation is absorbed by the photoresist material 60. The non-absorption of the out-of-band radiation allows the patterned photoresist layer 60A to have more clearly-defined (or sharper or crisper) patterns, such as the opening 80. In other words, pattern contrast and imaging performance is enhanced.

After the patterned photoresist layer 60A is formed, one or more fabrication processes such as an etching process or an implantation process may be performed, using the patterned photoresist layer 60A as a mask. Thereafter, the patterned photoresist layer 60A may be removed by a photoresist removal process known in the art, such as a stripping or an ashing process.

Figure 4:
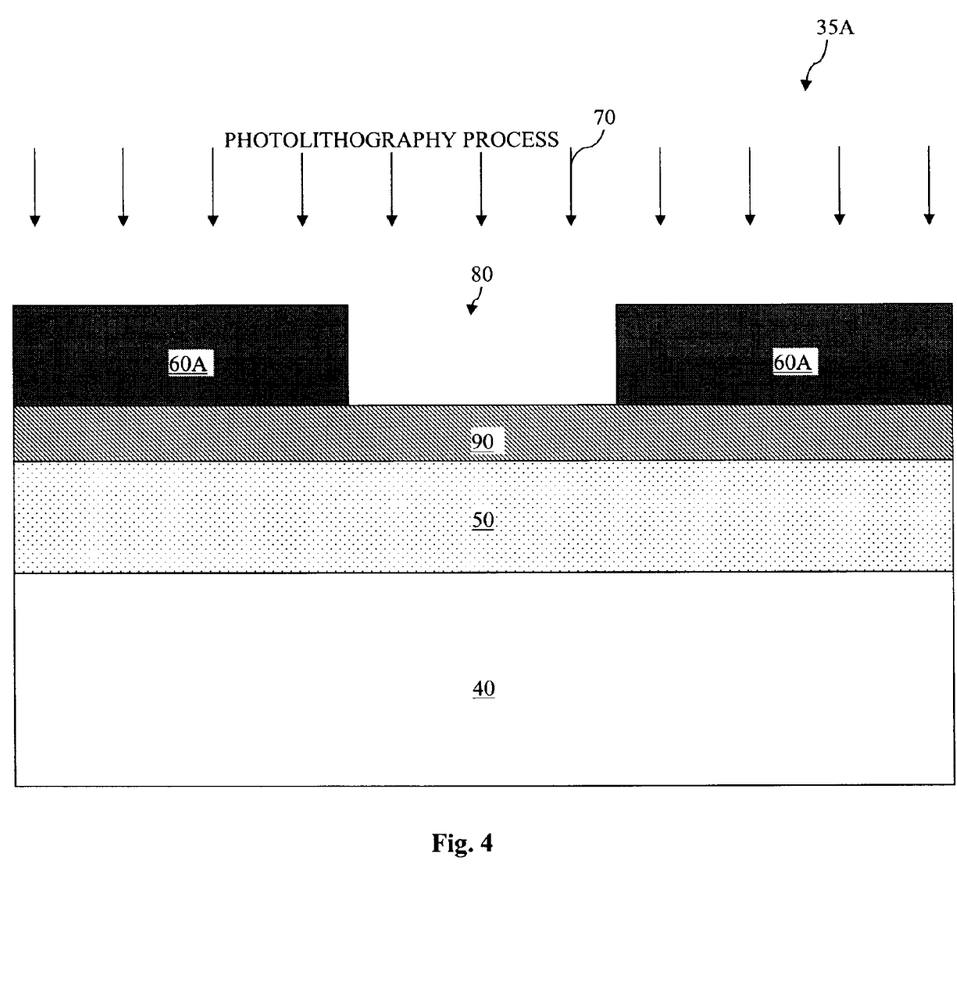

FIG. 4 illustrates a diagrammatic fragmentary cross-sectional side view of a semiconductor device 35A at a stage of fabrication in accordance with an alternative embodiment of the present disclosure. For purposes of consistency and clarity, similar features are labeled the same throughout FIGS. 2-4. Referring to FIG. 4, an anti-reflective coating (ARC) layer 90 is formed on the substrate 50 before the photoresist layer 60 is formed. In an embodiment, the ARC layer 90 is formed immediately below the photoresist layer 60. The ARC layer 90 includes a material that absorbs the out-of-band radiation in the EUV lithography process discussed above. This means that the material of the ARC layer 90 may substantially absorb radiation having wavelengths in a range from about 140 nm to about 400 nm. As such, the ARC layer 90 helps prevent the reflected out-of-band radiation from being absorbed (however little) by the photoresist material 60. Stated differently, out-of-band radiation that transmitted through the photoresist material 60 may be reflected by the substrate 50 back toward the photoresist material 60. The ARC layer 90 will substantially absorb this reflected out-of-band radiation, thereby preventing the radiation to be absorbed by the photoresist material 60, even though the absorption rate by the photoresist material 60 would have been low. In an embodiment, the Light absorbance Materials (LAM) disclosed in U.S. Pat. No. 7,459,260 is used to implement the ARC layer 90.

Figure 5:
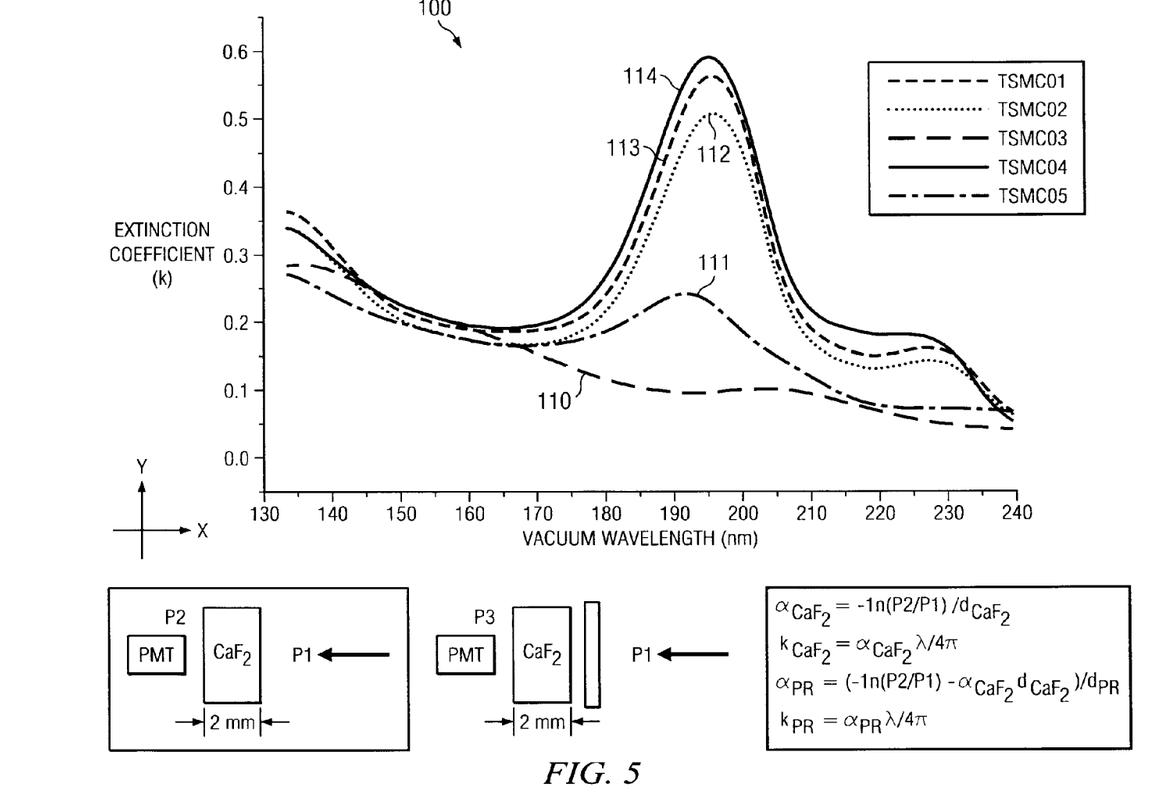
FIG. 5 is a graph illustrating the radiation-absorption rates across different bandwidths for various photoresist materials.

FIG. 5 is a graph 100 that illustrates the experimental results of radiation-absorption rates for various photoresist materials (TSMC01, TSMC02, TSMC03, TSMC04, and TSMC05) at various wavelengths. These photoresist materials are coated on the CaF2 substrate respectively. By using the α step, the thicknesses of these samples are 65 nm. By employing the "Beamline 08" at NSRRC (National Synchrotron Radiation Research Center, Taiwan), the optical power was measured vs. free-space wavelength for these samples and the CaF2 substrate. With the gathered above data, transmittances were calculated for these samples, and from the formulas shown in FIG. 5, the absorption coefficients were obtained for these photoresist materials. In more detail, an X-axis of the graph 100 denotes a range of wavelengths from 130 nm to 310 nm (though FIG. 5 only illustrates up to 240 nm). A Y-axis of the graph 100 denotes radiation absorbance from 0 to 2.5 (though FIG. 5 only illustrates up to 0.65). The graph 100 includes five different photoresist materials, whose absorbance VS radiation wavelength performances are represented by curves 110, 111, 112, 113 and 114, respectively. The photoresist material represented by the curves 110 and 111 are manufactured according to the various aspects of the present disclosure, meaning that it does not include the phenyl, naphthyl, and anthrancenyl aromatic groups in their polymer. The photoresist material 111 has higher concentration of PAG than 110. The photoresist materials represented by the curves 112, 113 and 114 are different types of photoresist materials, and accordingly include at least one of the phenyl, naphthyl, and anthrancenyl aromatic groups in their polymer.

As the graph 100 illustrates, the radiation-absorption rate for the curve 110 is low for wavelengths near 200 nm and above. This is due to the absence of the phenyl, naphthyl, and anthrancenyl aromatic groups. In comparison, the radiation-absorption rates for the curves 112, 113, and 114 are still quite substantial between wavelengths of 200 nm to 300 nm. As discussed above, these wavelengths are considered out-of-band wavelengths for an EUV lithography process. The absorption of these out-of-band wavelengths will substantially reduce the contrast capabilities of the EUV lithography process and therefore result in poor imaging performance. In comparison, the curve 110 has lower absorption rates from 200 nm to 300 nm, and therefore its corresponding photoresist material has better imaging performance. Thus, one of the advantages offered by the present disclosure over conventional photoresist materials is better imaging performance due to non-absorption of out-of-band radiation. However, it is understood that different embodiments may offer different advantages, and that no particular advantage is necessarily required for all embodiments.

It is also understood that the graph 100 is shown merely for the purposes of providing examples. Other embodiments of the present disclosure may include photoresist materials having even better imaging performance with respect to the out-of-band radiation absorption rate. For example, another embodiment may include a photoresist material that has a substantially 0% radiation absorption rate from 140 nm to 200 nm.

One of the broader forms of the present disclosure involves a photoresist that includes: a polymer that is free of aromatic groups and a photo acid generator has less than three aromatic groups. In an embodiment, the PAG includes an anion component and a cation component. The anion component has one of following chemical formulas:

The cation component has one of the following chemical formulas:

Wherein $R^1$ includes a material selected from the group consisting of: hydrogen, fluorine, methyl, ethyl, and trifluoromethyl, and $R^2$ include a material selected from the group consisting of: an alkyl group, an alkenyl group, and an oxoalkyl group.

Another of the broader forms of the present disclosure involves a material that includes a photo acid generator (PAG) that contains less than three aromatic groups. The PAG includes: an anion component having one of following chemical formulas:

The PAG also includes a cation component having one of following chemical formulas:

$R^2$ and $R^2$ each represent a chemical compound.

Still another of the broader forms of the present disclosure involves a method of fabricating a semiconductor device that includes: providing a wafer; forming a photoresist material over the wafer, the photoresist material having a polymer that is free of a phenyl group, a naphthyl group, and an anthrancenyl group and a photo acid generator has less than three aromatic group; and patterning the photoresist material using an extreme ultraviolet (EUV) lithography process.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claims is:

1. An extreme ultraviolet (EUV) photoresist, comprising:
a polymer that is free of an aromatic group; and
a photo acid generator (PAG) free of aromatic groups,
wherein the PAG includes an anion component and a cation component,
wherein the anion component has one of the following chemical formulas:

and the cation component has a chemical formula:

wherein:
each $R^1$ independently includes a material selected from the group consisting of: methyl and ethyl; and
each $R^2$ independently includes a material selected from the group consisting of: an alkyl group, an alkenyl group, and an oxoalkyl group.

2. The EUV photoresist of claim 1, wherein at least two of $R^2$ are bonded together to form a ring with $S^+$.

3. The EUV photoresist of claim 1, wherein the alkyl group, the alkenyl group, and the oxoalkyl group are straight.

4. The EUV photoresist of claim 1, wherein the alkyl group, the alkenyl group, or the oxoalkyl group is branched.

5. The EUV photoresist of claim 1, wherein the polymer includes recurring units that each have a chemical formula selected from the group consisting of:

wherein:
each $R^1$ independently includes a material selected from the group consisting of: hydrogen, fluorine, methyl, ethyl, and trifluoromethyl;
each $R^3$ independently includes a material selected from the group consisting of: a labile group, hydrogen, a fluoroalkyl group, a fluoroalcohol-containing substituent group, and combinations thereof; and
each $R^4$ independently includes a lactone-structure-containing substituent group.

6. The EUV photoresist of claim 5, wherein the EUV photoresist is a negative photoresist.

7. A photoresist, comprising:
a photo acid generator (PAG) that contains less than three aromatic group; and
a polymer free of aromatic groups bonded to the PAG, wherein the PAG includes:
an anion component having one of the following chemical formulas:

and a cation component having one of the following chemical formulas:

wherein each $R^1$ is independently selected from the group consisting of methyl and ethyl, and
wherein each $R^2$ is independently selected from the group consisting of an alkyl group, an alkenyl group, and an oxoalkyl group.

8. The photoresist of claim 7, wherein the photoresist is an EUV photoresist.

9. The photoresist of claim 7, wherein the photoresist is substantially non-absorptive of radiation having a bandwidth ranging from about 140 nanometers to about 400 nanometers.

10. The photoresist of claim 7, wherein the polymer contains no phenyl group, no naphthyl group, and no anthrancenyl group, and wherein the polymer includes recurring units having one of the following structural diagrams:

wherein:
each $R^1$ independently includes a material selected from the group consisting of: hydrogen, fluorine, methyl, ethyl, and trifluoromethyl;
each $R^3$ independently includes a material selected from the group consisting of: labile group, hydrogen, a fluoroalkyl group, a fluoroalcohol-containing substituent group, and combinations thereof; and
each $R^4$ independently includes a lactone-structure-containing substituent group.

11. A method of fabricating a semiconductor device, comprising:
providing a wafer having a material layer formed thereon;
forming a layer of a photoresist material over the material layer on the wafer, the photoresist material having a polymer that is free of an aromatic group and a photo acid generator (PAG) that has less than three aromatic groups wherein the forming the photoresist material is carried out in a manner such that the polymer is free of aromatic group and the PAG includes an anion component and a cation component, wherein the anion component has one of the following chemical formulas:

and the cation component has one of following chemical formulas:

wherein each $R^1$ independently includes a material selected from a group consisting of methyl and ethyl and each $R^2$ independently includes a material selected from a group consisting of an alkyl group, an alkenyl group, and an oxoalkyl group; and
patterning the photoresist material using an lithography process.

12. The method of claim 11, wherein the photoresist material is substantially non-absorptive of out-of-band radiation and the lithography process is an EUV lithography process.

13. The method of claim 12, wherein the out-of-band radiation includes radiation having a bandwidth ranging between about 140 nanometers and about 400 nanometers.

14. The method of claim 11, wherein the alkyl group, the alkenyl group, and the oxoalkyl group are straight.

15. The method of claim 11, wherein the alkyl group, the alkenyl group, and the oxoalkyl group are branched.

16. The method of claim 11, wherein the polymer is free of a phenyl group, a naphthyl group, and an anthrancenyl group.

17. The method of claim 11, wherein the polymer includes recurring units that each have a chemical formula selected from the group consisting of:

wherein:

each $R^1$ independently includes a material selected from the group consisting of: hydrogen, fluorine, methyl, ethyl, and trifluoromethyl;

each $R^3$ independently includes a material selected from the group consisting of: a labile group, hydrogen, a fluoroalkyl group, a fluoroalcohol-containing substituent group, and combinations thereof; and each $R^4$ independently includes a lactone-structure-containing substituent group.

18. The method of claim 11, further including, before the forming a layer of a photoresist material over the material layer on the wafer, forming an anti-reflective coating (ARC) layer over the wafer.

19. The method of claim 18, wherein the ARC layer includes a material that absorbs radiation having a bandwidth in a range from about 140 nanometers to about 400 nanometers.

20. The EUV photoresist of claim 1, wherein the EUV photoresist is a negative photoresist.

* * * * *